United States Patent [19]
Wolf, Jr. et al.

[11] Patent Number: 5,290,221
[45] Date of Patent: Mar. 1, 1994

[54] SYSTEMS FOR ERADICATING CONTAMINANTS USING PHOTOACTIVE MATERIALS IN FLUIDS LIKE BLOOD

[75] Inventors: Ludwig Wolf, Jr., Inverness; John T. Foley, Wheeling; William R. Bratten, Lake Villa, all of Ill.

[73] Assignee: Baxter International Inc., Deerfield, Ill.

[21] Appl. No.: 994,094

[22] Filed: Dec. 17, 1992

Related U.S. Application Data

[63] Continuation of Ser. No. 630,863, Dec. 20, 1990, abandoned.

[51] Int. Cl.[5] ............................................. C12N 7/00
[52] U.S. Cl. ............................................ 604/4; 604/20
[58] Field of Search .................. 604/4, 5, 6, 20, 19, 604/27, 28; 210/748; 422/44

[56] References Cited

U.S. PATENT DOCUMENTS

| | | |
|---|---|---|
| 2,308,516 | 1/1943 | Knott . |
| 4,181,128 | 1/1980 | Swartz . |
| 4,321,919 | 3/1982 | Edelson . |
| 4,398,906 | 8/1983 | Edelson . |
| 4,402,318 | 9/1983 | Swartz ............................ 604/20 |
| 4,428,744 | 1/1984 | Edelson . |
| 4,456,512 | 6/1984 | Bieler et al. ................... 210/748 |
| 4,573,962 | 3/1986 | Troutner . |
| 4,612,007 | 9/1986 | Edelson . |
| 4,613,322 | 9/1986 | Edelson . |
| 4,683,889 | 8/1987 | Edelson . |
| 4,684,521 | 8/1987 | Edelson . |
| 4,705,498 | 11/1987 | Goss . |
| 4,708,715 | 11/1987 | Troutner et al. . |
| 4,727,027 | 2/1988 | Wiesehahn et al. . |
| 4,737,140 | 4/1988 | Lee et al. . |
| 4,769,131 | 9/1988 | Noll et al. ....................... 210/748 |
| 4,775,625 | 10/1988 | Sieber . |
| 4,822,335 | 6/1989 | Kawai et al. . |
| 4,831,268 | 5/1989 | Fisch et al. . |
| 4,838,852 | 6/1989 | Edelson et al. ................. 604/4 |
| 4,878,891 | 11/1989 | Judy et al. . |
| 4,889,129 | 12/1989 | Dougherty et al. . |
| 4,915,638 | 4/1990 | Sieber . |
| 4,921,473 | 5/1990 | Lee et al. . |
| 4,944,883 | 7/1990 | Schoendorfer et al. ........ 210/782 |
| 4,950,225 | 8/1990 | Davidner et al. . |
| 4,983,307 | 1/1991 | Nesathurai ..................... 210/748 |
| 5,030,200 | 7/1991 | Judy et al. ...................... 604/5 |
| 5,032,241 | 7/1991 | Robertson et al. ............ 210/748 X |
| 5,069,885 | 12/1991 | Ritchie ........................... 210/748 X |
| 5,078,673 | 1/1992 | Abrams . |

FOREIGN PATENT DOCUMENTS 0138489 6/1985 European Pat. Off. .
92903137.5 7/1993 European Pat. Off. .

OTHER PUBLICATIONS

Matthews et al., "Photodynamic Therapy of Viral Contaminants with Potential for Blood Banking Applications", *Transfusion*, v. 28,1 1988 pp. 81-83.

*Primary Examiner*—Robert A. Hafer
*Assistant Examiner*—Sam Rimell
*Attorney, Agent, or Firm*—Bradford R. L. Price; Paul C. Flattery; Daniel D. Ryan

[57] ABSTRACT

Systems for treating a fluid carrying a contaminant to which a photoactive material has been bound include a treatment device that defines a relatively narrow, arcuately shaped flow path. These systems envelop the path with a radiation chamber that directs radiation from one or more sources into the fluid.

15 Claims, 13 Drawing Sheets

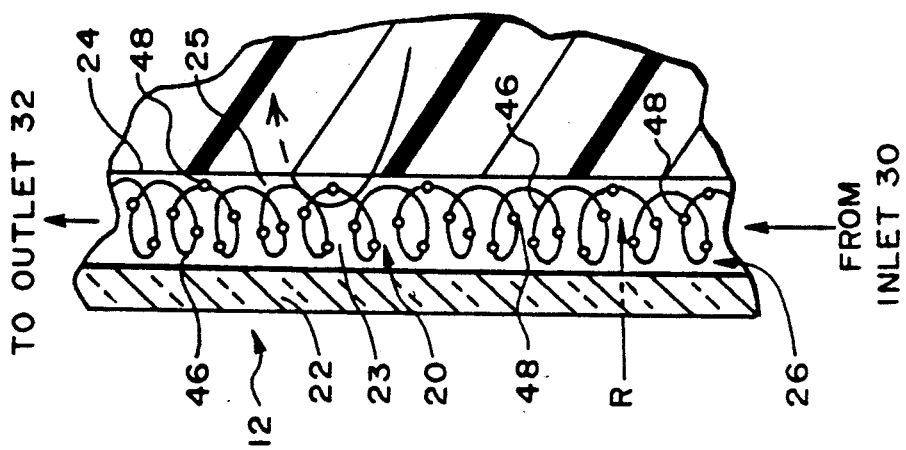
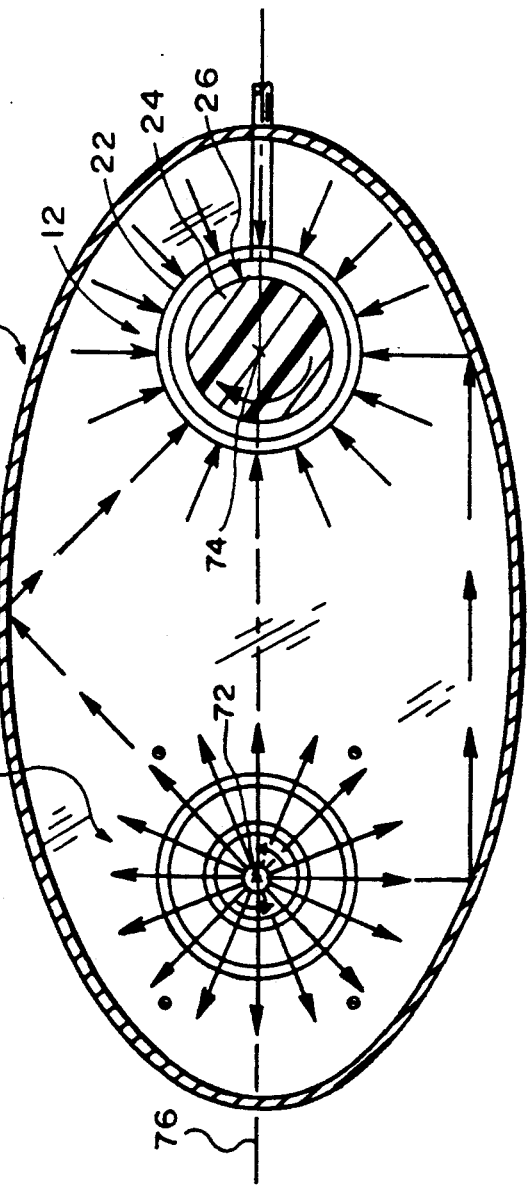
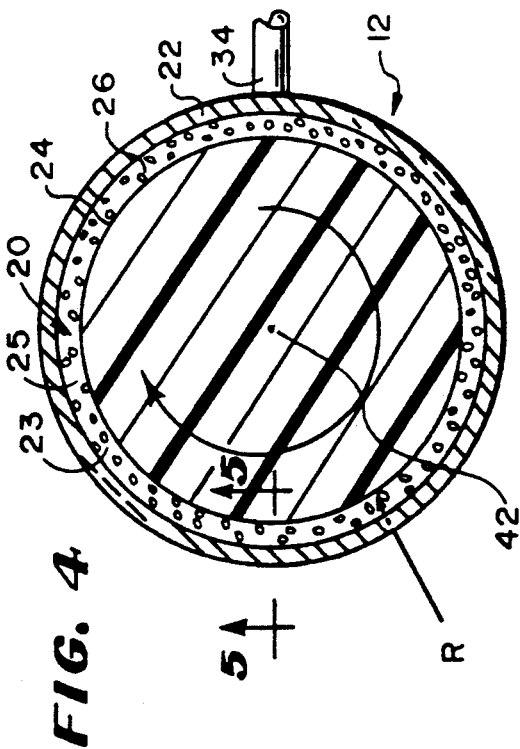

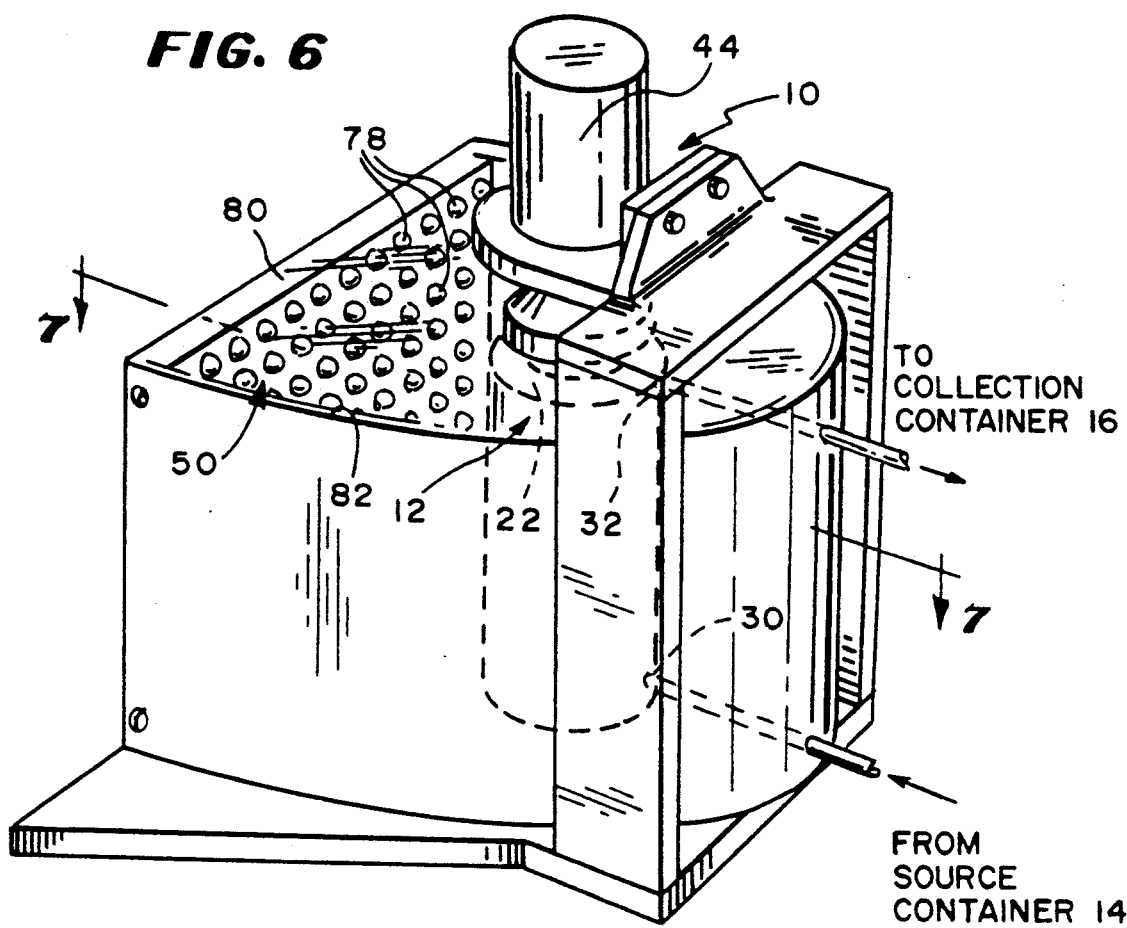
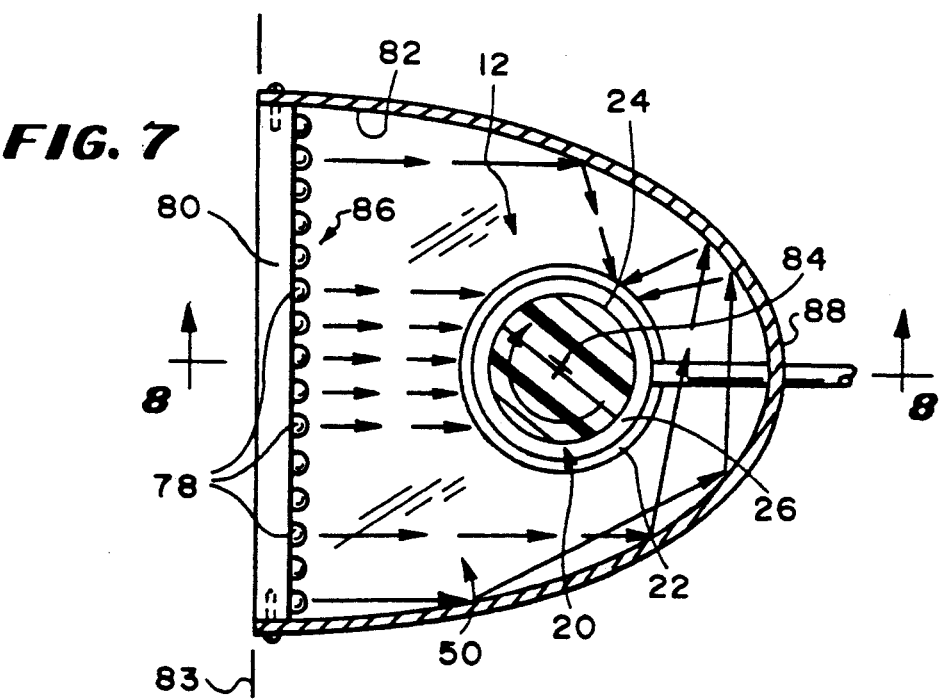

SYSTEMS FOR ERADICATING CONTAMINANTS USING PHOTOACTIVE MATERIALS IN FLUIDS LIKE BLOOD

This is a continuation of copending application Ser. No. 07/630,863, filed on Dec. 20, 1990, now abandoned.

FIELD OF THE INVENTION

The invention generally relates to the eradication of biological contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immunodeficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components prior to storage and transfusion. See Matthews et al, "Photodynamic Therapy of Viral Contaminants With Potential for Blood Bank Applications," Transfusion, 28(1), pp. 81-83 (1988). Various extracorporeal systems have been proposed that use photodynamic therapy to treat blood prior to storage and transfusion. See, for example, Edelson U.S. Pat. Nos. 4,613,322 and 4,684,521; Troutner et al 4,708,715; Wiesehahn et al 4,727,027; Sieber 4,775,625 and 4,915,683; and Judy et al 4,878,891.

To date, there has been a general lack of success in economically adapting the benefits of photodynamic therapy to the demands of the blood banking industry. The extracorporeal systems proposed to date have not been able to provide acceptable levels of eradication at the relatively high flow rates required to economically process therapeutic units of blood components.

For this and other reasons, the promise of photodynamic therapy in treating the nation's banked blood supply has gone largely unfulfilled.

SUMMARY OF THE INVENTION

The inventors have discovered that systems can be provided that accommodate relatively high processing flow rates and yet achieve an acceptably high rate of contaminant eradication through photodynamic therapy. The invention provides systems that convey the fluid during photodynamic treatment through a relatively narrow, arcuately shaped flow path. These systems envelop the path with a radiation chamber that directs radiation from one or more sources into the fluid.

One embodiment of the invention houses a treatment chamber within a generally flexible container. These systems wrap the flexible container about a generally cylindrical center platen to shape the treatment chamber into a relatively narrow, arcuately shaped gap. Another embodiment provides systems that use a generally rigid, cylindrical outer wall to house a treatment chamber. In this embodiment, a generally cylindrical inner wall occupies most of the interior area of the housing. The inner wall is spaced a short distance from the outer housing wall. This arrangement creates a treatment chamber within the housing that takes the shape of a relatively narrow, arcuate gap.

In each embodiment, the outer wall of the arcuate treatment chamber is essentially transparent to the radiation used to treat the fluid, to thereby pass the radiation into the fluid.

In each embodiment, the systems further include an associated radiation chamber that receives the treatment chamber and directs radiation uniformly upon the outer wall about its entire periphery.

In one arrangement, the system uses a single source of radiation positioned outside and on one side of the treatment chamber. To direct radiation from the single source into the chamber, the system envelops both the chamber and the source with a reflective surface that is generally elliptical in shape. The radiation source is located at one of the focal points of the ellipse. The chamber is located at the other focal point. Radiation emitted by the source is thereby transmitted by reflection uniformly into all sides of the arcuate flow gap, including those that do not directly face the radiation source.

In another arrangement, the system uses a number of discrete radiation sources. In one variation of this arrangement, the radiation sources are arranged in an array or bank at one end of an elliptical reflective surface. In this arrangement, the treatment chamber is located at the other end of the elliptical reflective surface near a focal point. Radiation emitted by the radiation bank is thereby transmitted by reflection uniformly into all sides of the flow gap.

In another variation of this arrangement, the radiation sources are arranged in panels that surround the housing.

In a preferred embodiment, the multiple radiation sources comprise photodiodes.

Another aspect of the invention also houses the treatment chamber within a generally flexible container. This aspect of the invention provides a generally elongated radiation source. In this arrangement, the radiation source is surrounded by a first generally cylindrical platen. A second generally cylindrical platen nests upon the first platen. The flexible container is wrapped about the first platen. The container is captured between the two nested platens, thereby conforming to their generally cylindrical shape. This creates the relatively narrow, arcuately shaped gap. The width of the treatment gap is determined by the spacing between the two nested platens.

The first platen is essentially transparent to the emitted radiation. This platen thereby passes radiation from the source directly into one side of the treatment chamber. The second platen is made of a material that reflects the emitted radiation. This platen thereby retains the emitted radiation within the treatment chamber, directing radiation that passes out of the treatment chamber back into the chamber.

The systems that embody the features of the invention are applicable for use in environments where sterility and biologically closed system integrity must be maintained during processing. The systems and methods therefore readily lend themselves to blood processing applications. The systems that embody the features of the invention can quickly and effectively eradicate contaminants like infectious agents from fluids like blood.

Other features and advantages of the invention will be pointed out in, or will be apparent from, the drawings, specification and claims that follow.

DESCRIPTION OF THE DRAWINGS

FIG. 3 is a top section view of the system shown in FIG. 1 taken generally along line 3—3 in FIG. 2;

FIG. 4 is a top section view of the treatment chamber associated with the system shown in FIG. 1 taken generally along line 4—4 in FIG. 2;

FIG. 5 is an enlarged side sectional view of the treatment chamber associated with the system shown in FIG. 1 taken generally along line 5—5 in FIG. 4;

FIG. 6 is a perspective view of another system for treating fluids using photodynamic therapy that embodies the features of the invention;

FIG. 7 is a top sectional view of the system shown in FIG. 6 taken generally along line 7—7 in FIG. 6;

Figure 1:
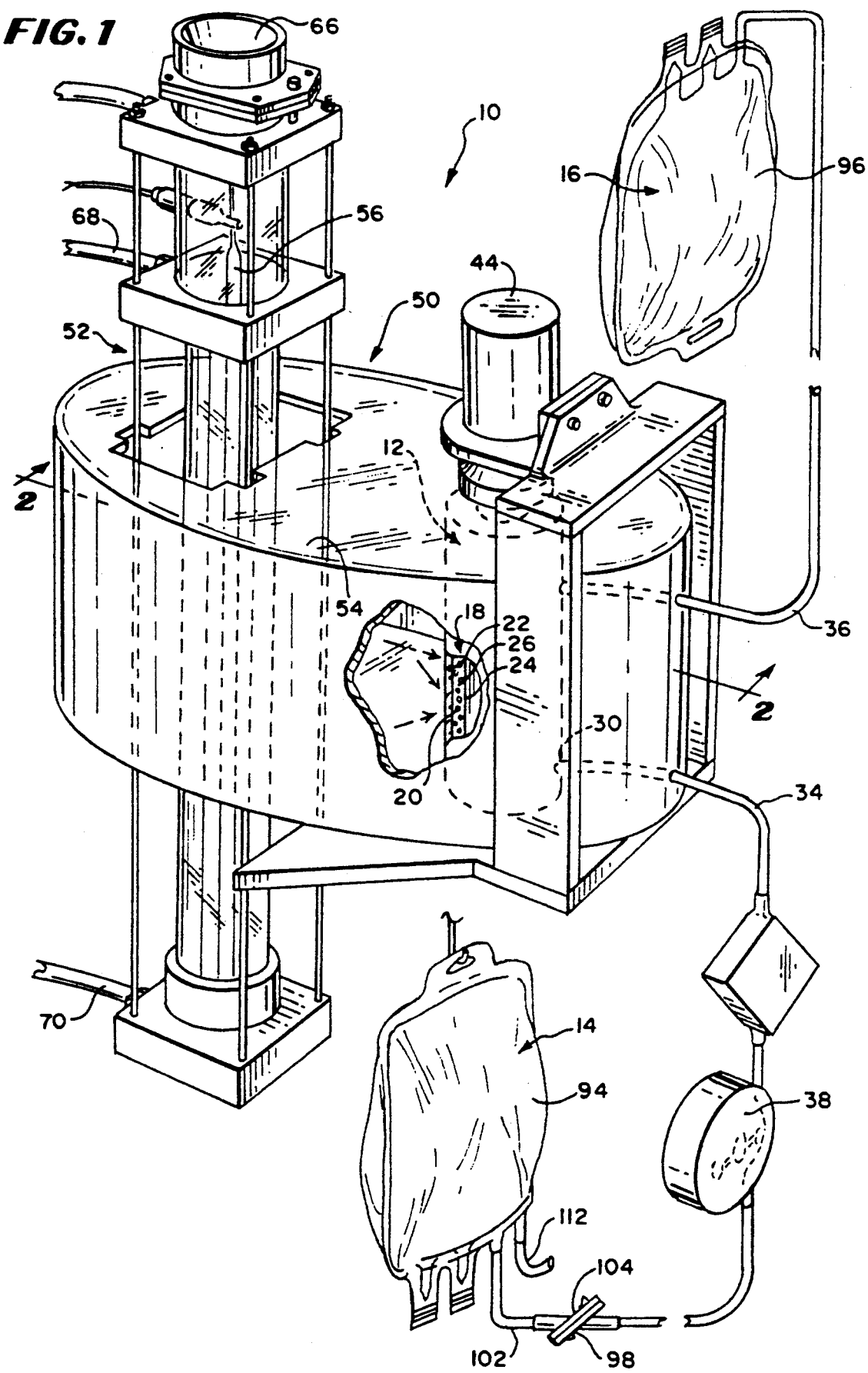
FIG. 1 is a perspective view, with portions broken away and in section of a system for treating fluids using photodynamic therapy that embodies the features of the invention.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a system 10 for treating a fluid carrying a biological contaminant that embodies the features of the invention. The system 10 includes a treatment device 12 that receives the fluid from a source container 14 and conveys the fluid after treatment to a collection container 16.

The fluid to be treated can vary. In the illustrated embodiment, the fluid comprises a component of whole human blood that is intended to be stored for transfusion. More specifically, the fluid consists of red blood cells suspended in plasma. Typically, a quantity of white blood cells is also present with the red blood cells. The fluid can also include an anticoagulant and, optionally, a storage medium for the blood component. Alternatively, the fluid can consist of platelets suspended in plasma.

In the illustrated embodiment, the contaminant comprises a pathogenic virus typically carried in the blood. For example, the contaminant can consist of the hepatitis-B virus; the human immunodeficiency virus; the Herpes virus; or the influenza virus.

The fluid in the source container 14 includes a photoactive material that has an affinity for the biological contaminant carried by the fluid. The photoactive material is added to the blood contained in the source container 14 after the blood is collected from a donor. The step of adding the photoactive material will be described in greater detail later.

Due to its affinity for the contaminant, the photoactive material becomes bound to the contaminant within the source container 14. The photoactive material is of a type that becomes active by exposure to radiation within a prescribed wavelength range. When activated by radiation, the material eradicates the contaminant.

Various types of photoactive materials can be used. In the illustrated embodiment, the photoactive compound comprises a family of light-activated drugs derived from benzoporphyrin. These derivatives are commonly referred as BPD's. BPD's are commercially available from Quadra Logic Technologies, Inc., Vancouver B.C., Canada.

BPD's, like other types of hematoporphyrin materials, have an affinity for the cell walls of many viral organisms that are carried in blood. They therefore bind or attach themselves to the biological cell wall of these organisms. When exposed to radiation, BPD's undergo an energy transfer process with oxygen, forming a singlet oxygen. When the singlet oxygen oxidizes, it kills the biological cells to which it has attached. BPD's are described in greater detail in Judy et al U.S. Pat. No. 4,878,891.

According to the invention, the system 10 conveys the fluid during photodynamic treatment through a relatively narrow, arcuately shaped flow path. The system 10 also envelops the path with a radiation chamber that uniformly directs radiation from one or more sources into the arcuate gap.

The arcuate gap can be formed in various ways. The drawings show several alternative embodiments. In FIGS. 1 to 14, the gap is preformed with a rigid housing. In FIGS. 15 to 22, the gap is created within the confines of a flexible container.

The first embodiment will now be described. As FIGS. 1 and 2 best show, the treatment device 12 includes a housing 18 that defines a treatment chamber 20. The housing 18 has a generally rigid tubular outer wall 22.

The housing 18 also contains a generally rigid interior wall 24. In the illustrated embodiment, the inner wall 24 takes the shape of a generally cylindrical rotor or spinner 24. This arrangement creates a preformed, relatively narrow, arcuate gap 26 between the rotor wall 24 and the interior of the housing wall 22. The preformed arcuate gap 26 creates the confines of the treatment chamber 20.

The housing wall 22 is made from a material that is essentially transparent to the radiation to thereby pass the radiation into the arcuate gap 26. This is shown by the arrow labeled with the letter R in FIGS. 4 and 5).

The fluid to be treated traverses the gap 26 between an inlet 30 and an outlet 32. The inlet 30 leads from the source container 14 through inlet tubing 34. The outlet 32 leads to the collection container 16 through outlet tubing 36. A pump 38 conveys fluid through the inlet tubing 34.

Figure 2:
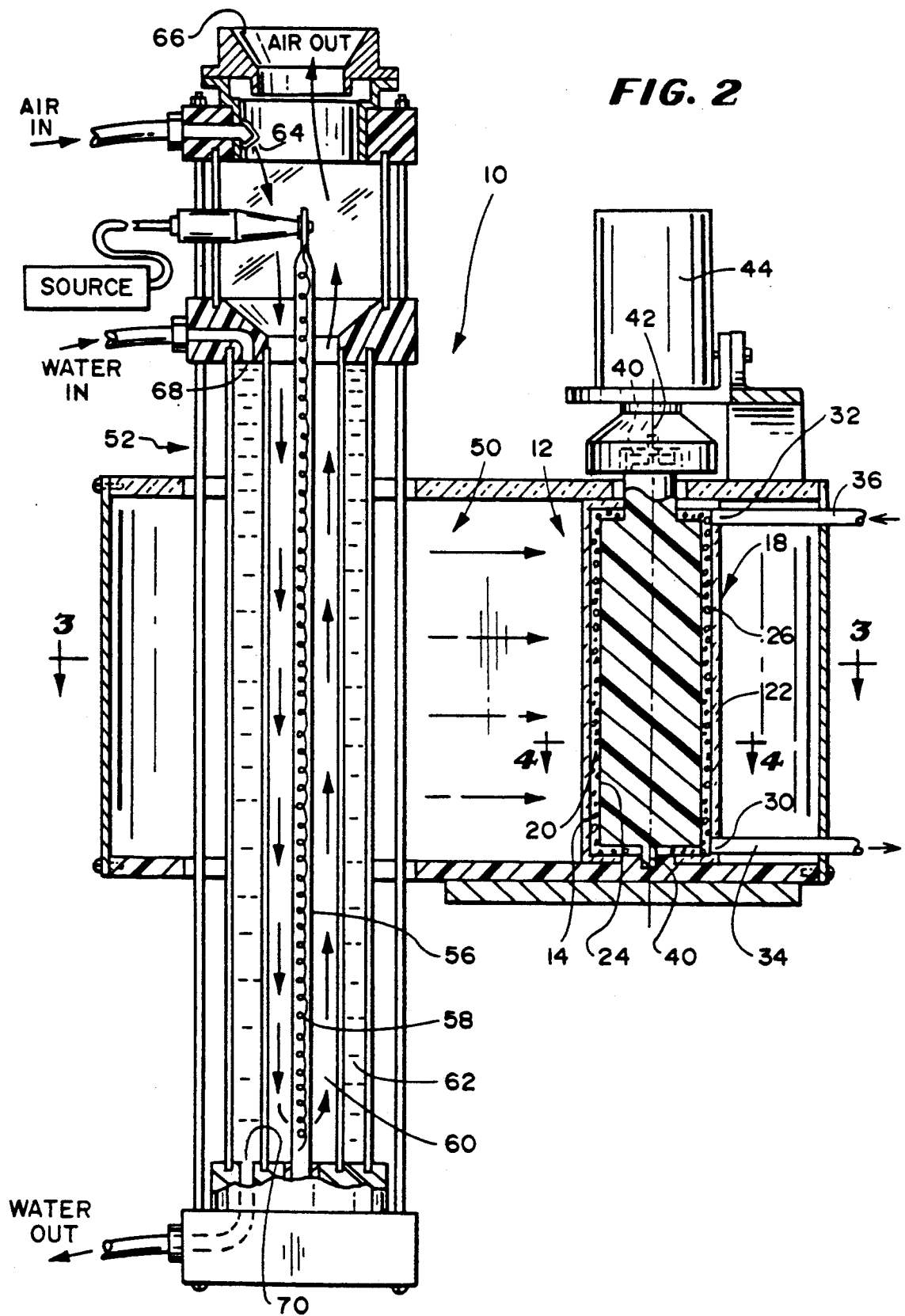
FIG. 2 is a side section view of the system shown in FIG. 1 taken generally along line 2—2 in FIG. 1.

In the illustrated embodiment, bearings 40 carry the spinner 24 for rotation within the housing 18 about an axis 42 that is generally parallel to the direction of fluid flow in the gap 26 (see FIG. 2). A drive 44 magnetically coupled to the spinner 24 rotates the spinner 24 at a controlled surface velocity.

By rotating the spinner 24 as fluid traverses the gap 26, the flow patterns within the gap 26 are significantly altered. The rotating spinner 24 creates secondary fluid flow patterns called vortices 46 within in the gap 26 (see FIG. 5). The vortices 46 spiral in a helical path along the axis of rotation 42. These vortices 46 are sometimes referred in the technical literature to as "Taylor Vortices" (see Taylor, "Stability of a Viscous Liquid Contained Between Two Rotating Cylinders", *Proc. of the Royal Society*, V151 (1935), pp. 289-343).

As FIG. 5 shows, the vortices 46 continually sweep the material carried by the fluid, including the contaminants to which the photoactive agent are bound (generally designated by numeral 48 in FIG. 5) from the inner region 25 of the treatment chamber 20 toward the outer region 23. Thus, the contaminants 48 not only follow an axial path between the inlet 30 and outlet 32 of the gap 26, but the contaminants 48 also follow a radial, spiraling path through the gap 26. The vortices 46 continually keep the contaminants 48 in circulation near the outer housing wall 22, where the radiation enters the gap 26. These mixing patterns established by the vortices 46 assure that all contaminants 48 carried by the fluid are continuously brought to the outer region of the gap 26 where the radiation enters the treatment chamber 20.

The use of these mixing patterns to further enhance exposure to radiation is described in greater detail in copending U.S. patent application entitled SYSTEMS AND METHODS FOR ERADICATING BIOLOGICAL CONTAMINANTS USING PHOTOACTIVE MATERIALS IN FLUIDS LIKE BLOOD.

In the illustrated embodiment, where the treated fluid contains blood materials, the gap 26 has a width of about 0.02 inch, and a length of about 3.0 inches The spinner 24 is rotated at about 3600 RPM's.

The treatment device 12 includes a radiation chamber 50 that directs radiation uniformly into the treatment chamber 20 (that is, into the gap 26). The radiation chamber 50 can be variously constructed. The drawings show three alternative constructions.

In the embodiment shown in FIGS. 1 to 3, the radiation chamber 50 includes a single source of radiation 52 and a reflector 54 that envelops both the radiation source 52 and the treatment device 12.

In this embodiment (as FIG. 2 best shows), the radiation source 52 comprises a tubular incandescent bulb 56 having an elongated filament 58. A power source (not shown) conveys electricity to the filament 58 to cause the filament 58 to emit radiation. The filament material is selected to emit radiation of a prescribed wavelength or range of wavelengths, according to the fluid that is to be treated.

In the illustrated embodiment, where the treated fluid contains red blood cells, filament 58 is made of tungsten. This material emits a band of radiation displaying a red color having a wavelength of about 690 nm. When operated at a voltage of about 250 volts (AC), the radiation emitted by the filament 58 has an intensity of about 1.4 mw/cm$^2$.

Red blood cells are essentially transparent to radiation at this wavelength. The BPD's, however, are not. The BPD's absorb radiation in this wavelength to become activated.

On the other hand, if the fluid to be treated contains platelets, the filament would be selected to have a wavelength displaying a blue color having wavelength of about 425 nm. Platelets are essentially transparent to radiation at this wavelength, but the BPD's are not.

The incandescent source 52 shown in FIGS. 1 to 3 includes first and second chambers 60 and 62 that concentrically surround the bulb 56. Fluids are circulated through these chambers 60 and 62 to cool the radiation source.

In the arrangement shown in FIGS. 1 to 3, pressurized air circulates from an inlet 64 through the first chamber 60. The air is vented through a chimney 66 from the top of the first chamber 60. A secondary cooling liquid like water circulates from an inlet 68 at the top of the second chamber 62. The cooling liquid exits the second chamber 62 through a bottom outlet 70.

In embodiment shown in FIGS. 1 to 3, the reflector 54 is generally elliptical in shape (as FIG. 3 best shows). The elliptical reflector 54 has two diametrically spaced focal points positioned 72 and 74 along its major axis 76. The filament 58 of the radiation source 52 is located at one focal point 72. The rotational axis 42 of the spinner 24 within the treatment chamber 20 is located at the other focal point 74.

In this arrangement, the entire interior surface of the reflector 54 is lined with a material that reflects the radiation emitted by the source 52. Gold or like highly reflective material can be used to reflect the wavelengths of radiation described above.

As FIG. 3 shows, the elliptical reflector 54 directs radiation emitted from the source uniformly around the exterior of the tubular housing 18 that surrounds the treatment chamber 20. Radiation uniformly fills the gap 26 of the treatment chamber 20 as the spinner 24 rotates to continuously mix the fluid as it traverses the gap 26 (as FIGS. 4 and 5 show).

In the second alternative embodiment (shown in FIGS. 6 to 9) the radiation chamber 50 includes a plurality of radiation sources (generally designated by the numeral 78). The treatment device 12 associated with this embodiment is the same as the one associated with the embodiment shown in FIGS. 1 to 3 (the interior of which in use is also shown in FIGS. 4 and 5).

In the illustrated embodiment (see FIGS. 6 and 9), each radiation source 78 is "discrete," meaning that each source 78 is a self-contained emitter of radiation that establishes its own zone of radiation. Being discrete, each source 78 also is capable of operation to emit a radiation independent of the emission of radiation by the other sources 78.

In the illustrated embodiment, each radiation source 78 takes the form of a photodiode. As with the single radiation source 52, various types of photodiodes can be selected, depending upon the fluid to be treated and the characteristics of the photoactive material used. In the illustrated embodiment, where the treated fluid contains red blood cells, all the photodiodes use transparent substrate aluminum gallium arsenide material (TS AlGaAs). Photodiodes of this type are commercially available from Hewlett-Packard Co. (Product Designation "HLMP8150 15 Candella").

These photodiodes emit a band of radiation at a relatively narrow viewing angle of about 4 degrees. The prescribed band of radiation has a relatively precise wavelength displaying a red color having a peak wavelength of about 690 nm. As previously explained, if the fluid to be treated contains platelets, the photodiode would be selected to have a wavelength displaying a blue color having peak wavelength of about 425 nm.

In the illustrated embodiment, each discrete photodiode radiation source 78 has a minimum intensity of about 8.0 cd (at 20 mA), a maximum intensity of about 36.0 cd (at 20 mA), and a typical intensity of about 15.0 cd (at 20 mA). Each photodiode source 78 operates at a low maximum forward voltage of about 2.4 V.

Figure 9:
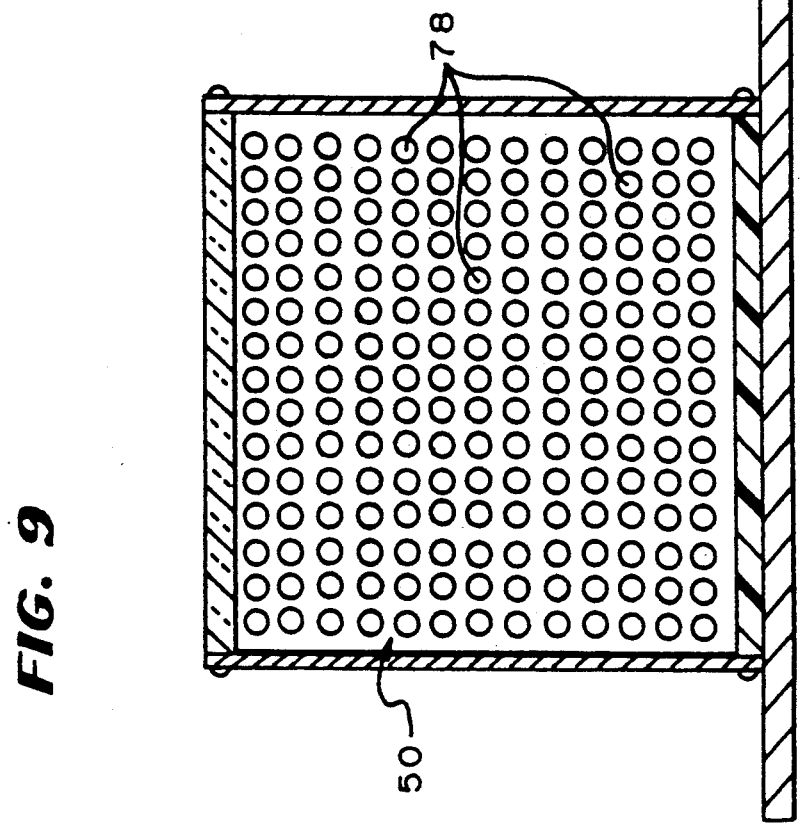
FIG. 9 is an elevation view of a portion of the system shown in FIG. 6 taken generally along line 9—9 in FIG. 8.
Figure 8:
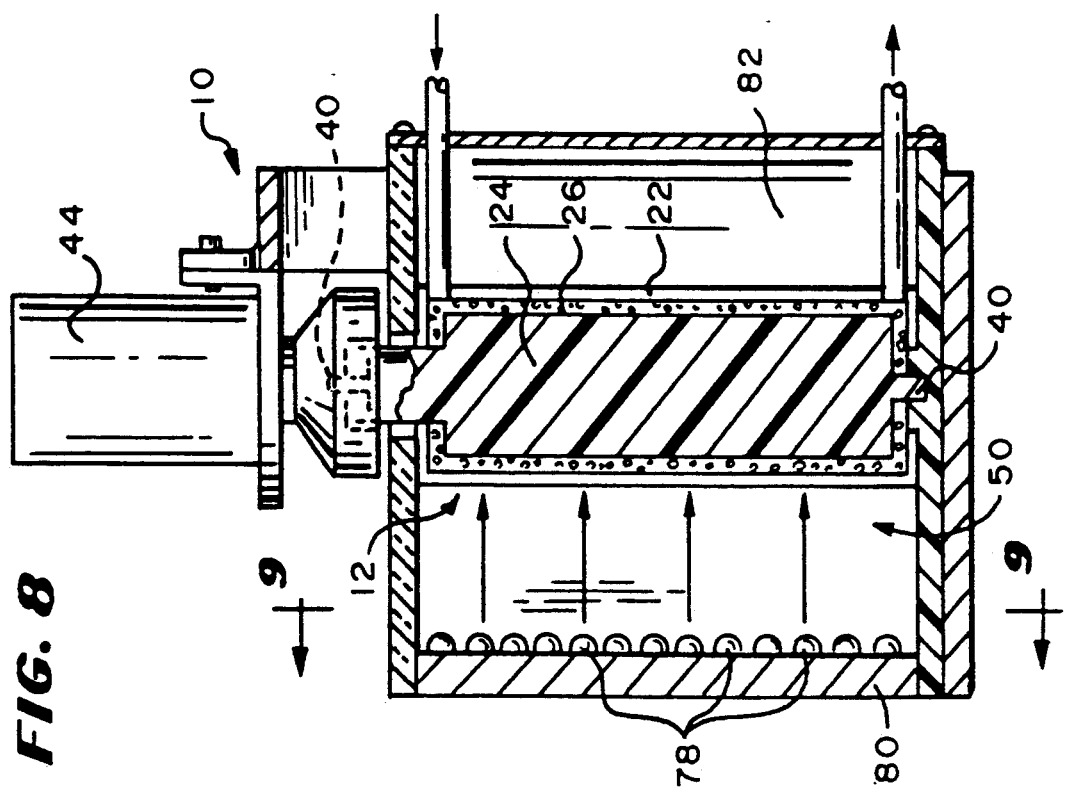
FIG. 8 is a side sectional view of the system shown in FIG. 6 taken generally along line 8—8 in FIG. 7.
Figure 10:
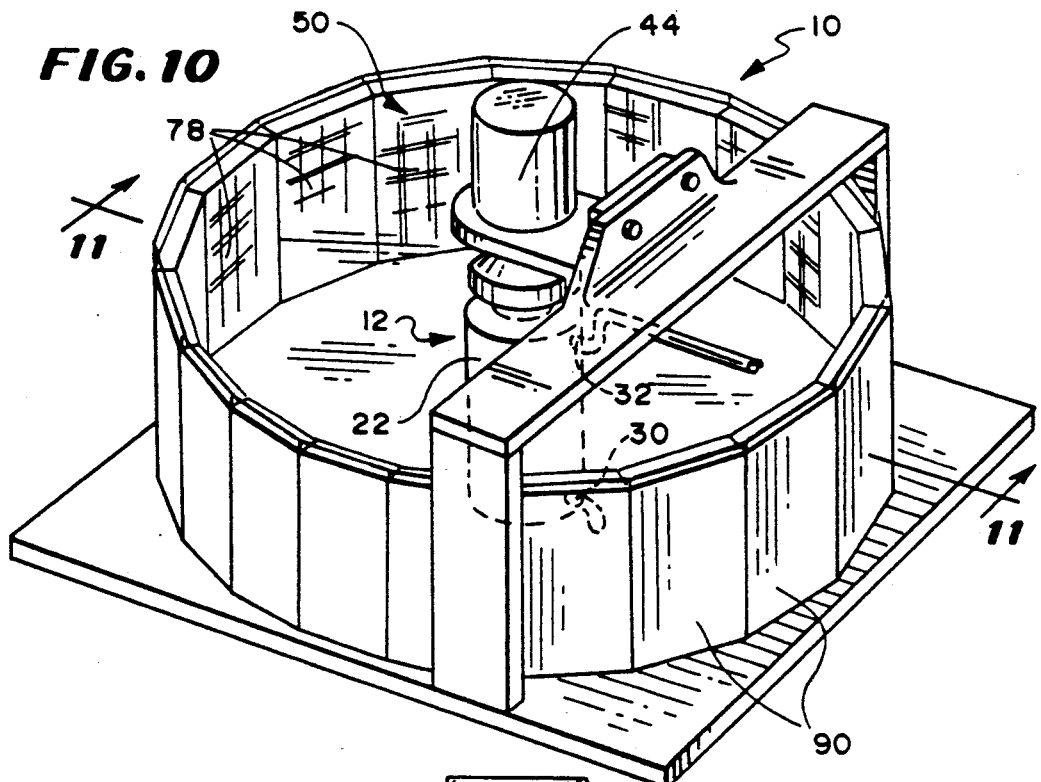
FIG. 10 is a perspective view of another system for treating fluids using photodynamic therapy that embodies the features of the invention.
Figure 11:
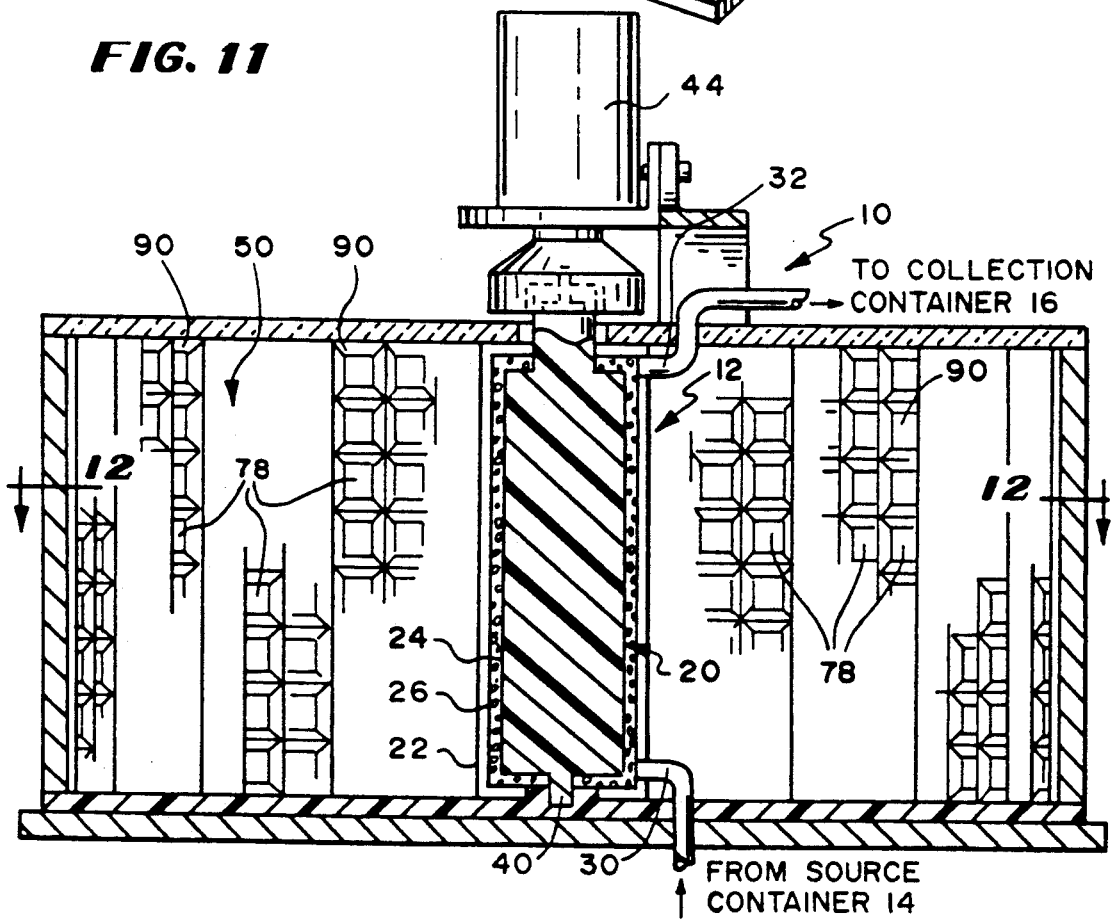
FIG. 11 is a side sectional view of the system shown in FIG. 10 taken generally along line 11—11 in FIG. 10.
Figure 13:
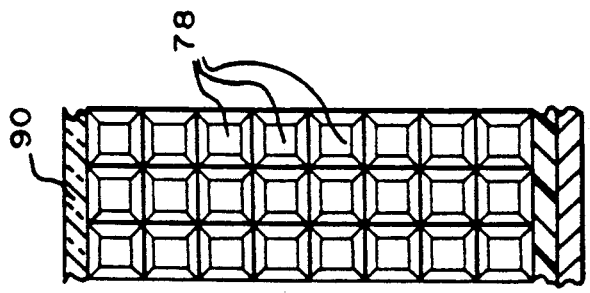
FIG. 13 is an elevation view of a portion of the system shown in FIG. 10 taken generally along line 13—13 in FIG. 12.
Figure 12:
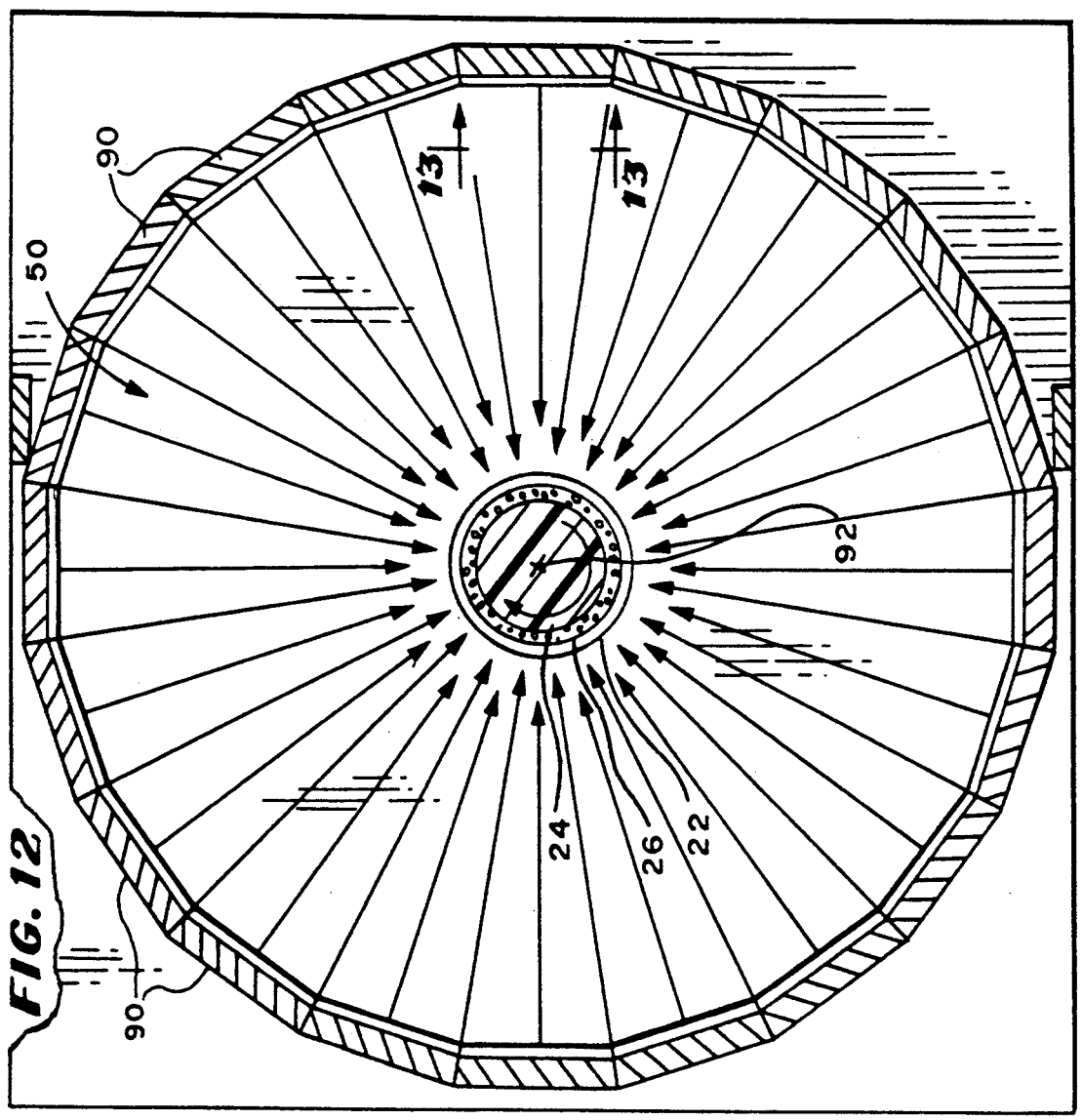
FIG. 12 is a top sectional view of the system shown in FIG. 10 taken generally along line 12—12 in FIG. 11.

In embodiment shown in FIGS. 6 to 9, the discrete radiation sources 78 are arranged in a bank 80 (as FIG. 9 best shows). The bank 80 includes the plurality of discrete sources 78 arranged in rows of about 15 sources each (shown horizontally in FIG. 6). In the illustrated embodiment, the bank 80 includes about 195 discrete radiation sources 78. A control element (not shown) operates the discrete radiation sources 78.

In this arrangement, the radiation chamber 50 also includes a reflector 82 that surrounds the treatment chamber 20. As FIG. 7 best shows, the reflector 82 generally conforms to the shape of an ellipse that has been truncated along its minor axis 83 and therefore has but a single focal point 84. The bank 80 of radiation sources is located across the open end 86 the truncated reflector 82. The rotational axis 42 of the treatment chamber 20 is located at the closed end 88 along focal point 84.

As in the embodiment shown in FIGS. 1 to 3, the entire interior surface of the reflector 82 is lined with a material like gold that reflects the radiation emitted by the source. As FIG. 7 shows, the reflector 82 directs radiation emitted from the bank 80 uniformly around the exterior of the tubular housing 18 of the treatment chamber 20. Radiation uniformly fills the gap 26 of the treatment chamber 20 as the spinner 24 rotates to mix the fluid traversing the gap 26.

In the third alternative embodiment (shown in FIGS. 10 to 13), like the embodiment shown in FIGS. 6 to 9, the radiation chamber 50 includes a plurality of radiation sources that take the form of photodiodes (which are also generally designated by the same numeral 78). Like the embodiment shown in FIGS. 6 to 9, the discrete radiation sources 78 are arranged in individual banks 90. However, unlike the arrangement shown in FIGS. 6 to 9, the treatment chamber 20 does not include a reflector. Instead, the banks 90 of radiation themselves completely surround the treatment chamber 20.

In the illustrated embodiment, there are twenty (20) banks 90 arranged circumferentially about a center point 92. The rotational axis 42 of the treatment chamber 20 generally lies along on this center point 92. Each bank 90 includes twenty-four (24) discrete light sources 78. The treatment chamber 20 is thereby exposed to some 480 discrete radiation sources 78. A control element (not shown) operates the discrete radiation sources 78.

As in the preceding embodiments, the enveloping banks 90 of radiation sources 78 direct radiation uniformly around the exterior of the tubular housing 18 of the treatment chamber 20. Radiation uniformly fills the gap 26 of the treatment chamber 20 as the spinner 24 is rotated to mix the fluid traversing the gap 26.

Because each radiation source 78 shown in the second and third alternative embodiment is discrete, the control element can be configured to operate two or more of the radiation sources at a different wavelength. Alternatively, the control element can be configured to operate two or more of the discrete sources 78 of radiation at substantially the same wavelength.

Furthermore, the zone of radiation emitted by each discrete source 78 can be varied, as can the intensity of radiation of each source 78.

In all the illustrated embodiments, the source container 14 and the collection container 16 each takes the form of a bag (respectively 94 and 96) made of a flexible inert plastic material, like plasticized medical grade polyvinyl chloride.

Figure 14:
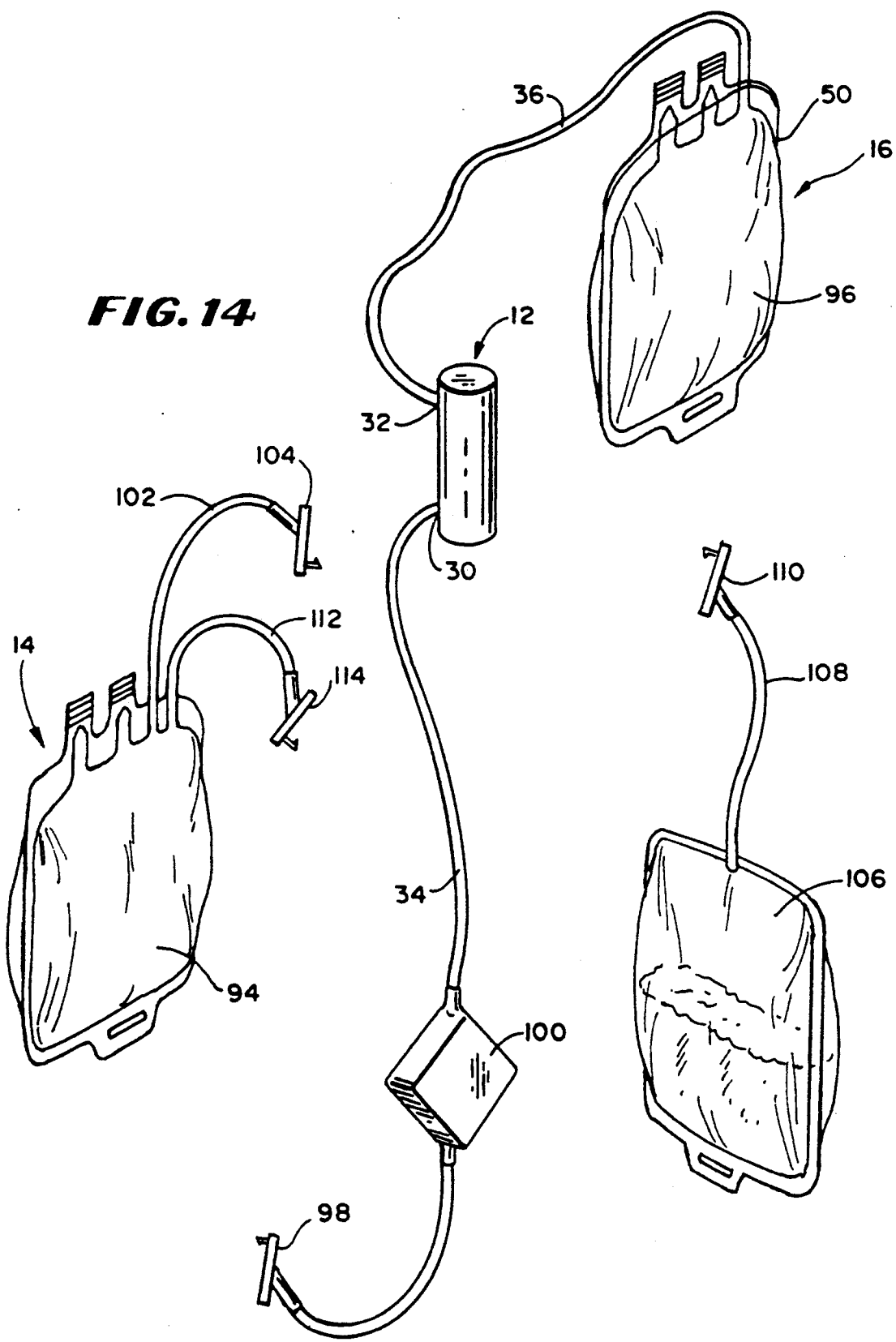
FIG. 14 is a perspective view of the treatment chamber and its associated components that the systems shown in FIGS. 1 to 13 incorporate, with the component disassembled as they would be prior to use.

In the illustrated embodiment (as FIG. 14 shows), the inlet 30 to the treatment device 12 includes the length of flexible inert plastic tubing 34. The tubing 34 terminates in a first connection device 98. The tubing 34 also includes a conventional inline filter 100 for removing the white blood cells from the fluid prior to entering the treatment device 12. The filtration medium used (not shown) can include cotton wool, cellulose acetate, or another synthetic fiber like polyester.

A length of flexible inert plastic tubing 102 also joins the source container 14. This tubing 102 includes a second connection device 104 that mates with the first connection device 98 to join the source container 14 to the inlet 30 of treatment device 12 (as FIG. 1 shows).

While various known connection devices may be used, in the illustrated embodiment, the devices 98 and 104 are preferable sterile connection devices like those shown in Granzow et al U.S. Pat. Nos. 4,157,723 and 4,265,280, which are incorporated herein by reference.

The outlet 32 of the treatment device 12 also includes the already described tubing 36. The end of the tubing 36 joins the collection container 16. In an alternative arrangement (not shown), the tubing 36 could be normally separated into two lengths, like tubings 34 and 102, each having a sterile connection device to join the collection container 16 to the outlet 32 of the treatment device 12 prior to use.

In the illustrated embodiment (as FIG. 14 shows), an auxiliary container 106 holds a solution containing the photoactive material. The auxiliary container 106 also includes a length of tubing 108 that carries with a third (preferably sterile) connection device 110. In this arrangement, the source container 14 also includes another length of tubing 112 that carries a fourth (preferably sterile) connection device 114. By joining the third and fourth sterile connection devices 110 and 114, the photoactive material can be conveyed from the auxiliary container 106 into the source container 14 for mixing with the fluid to be treated. The joined tubings 108 and 112 form a closed, internally sterile path for introducing the photoactive materially into the source container 14. Once the photoactive material has been transferred, the tubing 108 can be heat sealed closed downstream of the joined connection devices 110 and 114 (as FIG. 1 shows), and the auxiliary container 106 removed.

By using the sterile connection devices 98, 104, 110, and 114, the formed flow paths comprise a closed, internally sterile path for conveying fluid from the source container 14, through the treatment chamber 20, and into the collection container 16.

After treatment, the tubing 36 can be heat sealed closed and the collection container 16 removed for storage.

The various additional alternative embodiments shown in FIGS. 15 to 22 will now be described.

In this embodiment (see FIG. 15), the treatment chamber 20 is housed within the confines of a bag 116 made of a flexible inert plastic material that is essentially transparent to the treatment radiation. The bag 116 has heat sealed peripheral edges 118 to form a sealed interior area.

Figure 15:
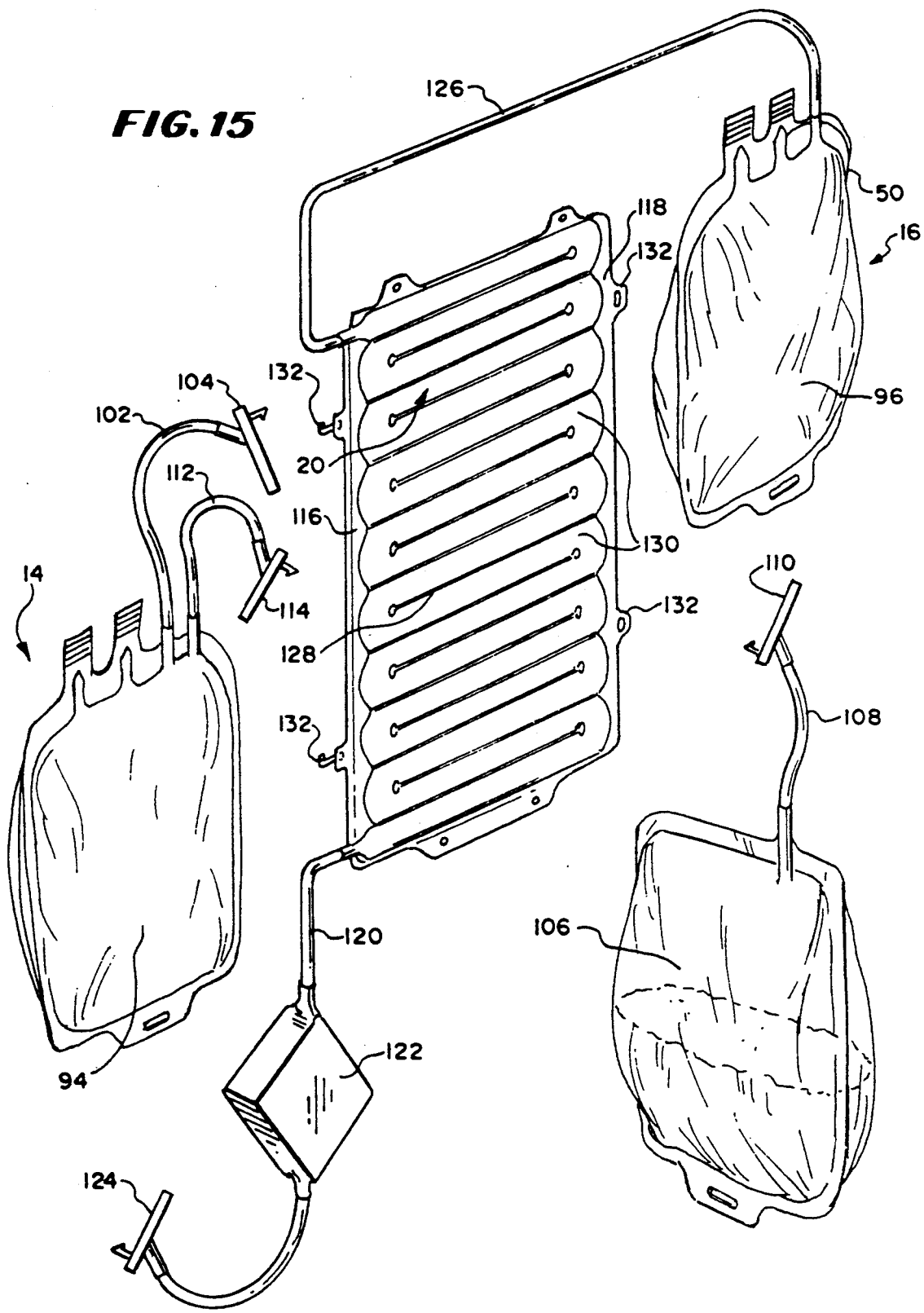
FIG. 15 is a perspective view of another embodiment of a treatment chamber and its associated components disassembled as they would be prior to use.

As FIG. 15 shows, the bag 116 includes an inlet tube 120 with an inline filter 122. The inlet tube 120 terminates in a connection device 124 that mates with the connection device 104 carried by the source container 14 in the manner previously described (as FIG. 14 shows).

The bag 116 also includes an outlet tube 126 that is attached to the collection container 16.

In the illustrated embodiment, the bag 116 further includes a series of interior heat sealed regions 128 that divide the interior area into interconnected flow passages 130.

Figure 16:
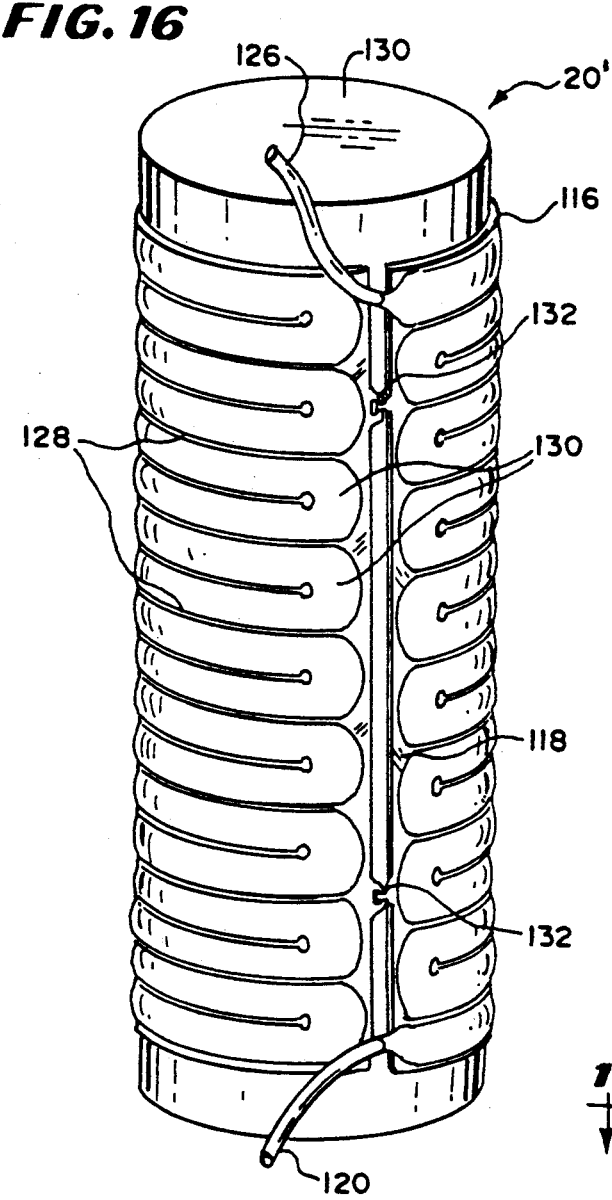
FIG. 16 is a perspective view of the treatment chamber shown in FIG. 15 wrapped around a center patten to form a treatment device.

As shown in FIG. 16, the bag 116 constitutes a component part of a treatment device 20'. The device 20' includes a generally cylindrical center platen 130 about which the bag 116 is wrapped. The bag 116 includes mating fasteners 132 on its side edges to hold the bag snugly against the platen 130.

Figure 17:
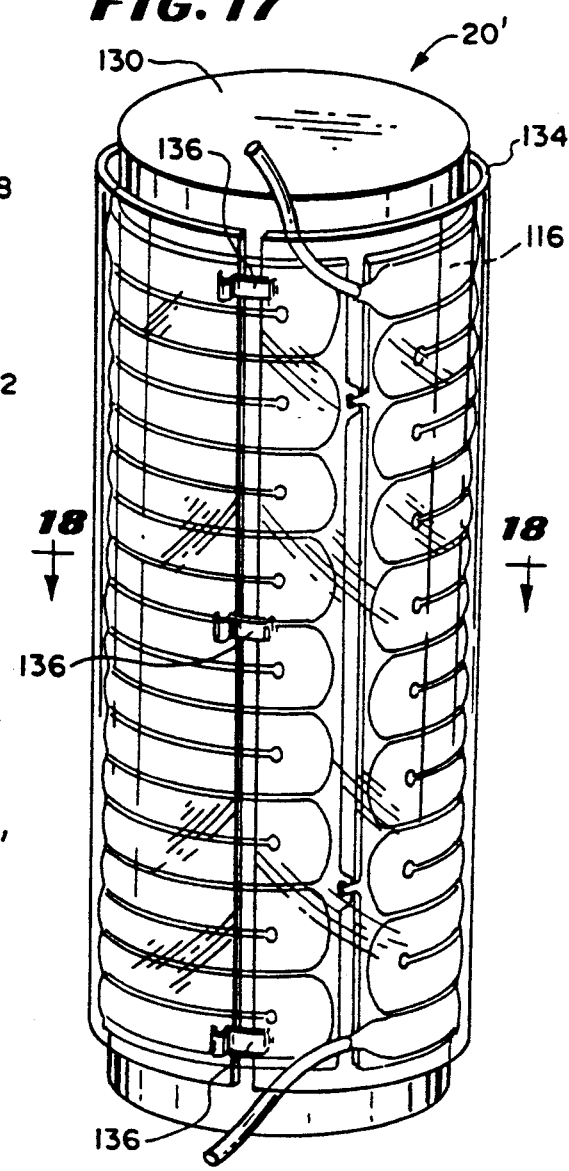
FIG. 17 is a perspective view of the treatment chamber shown in FIG. 15 captured between an inner and outer platen to form a treatment device.

In the embodiment shown in FIG. 17, a generally cylindrical outer platen 134 further nests about the center platen 130 to capture the bag 116 in between. Latches 136 hold the outer platen 134 closed. The outer platen 134 is made of a material that is essentially transparent to the treatment radiation.

Figure 18:
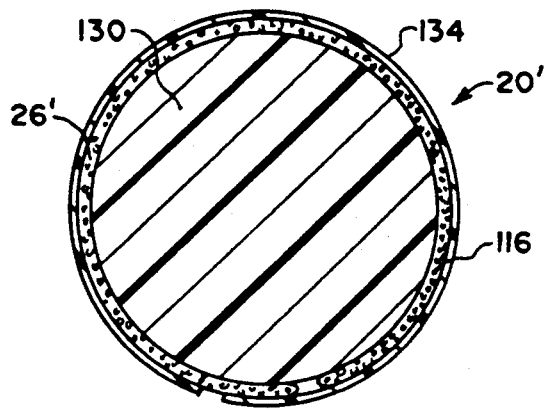
FIG. 18 is a top sectional view of the top portion of the treatment device shown in FIG. 17, taken generally along line 18—18 in FIG. 17.
Figure 19:
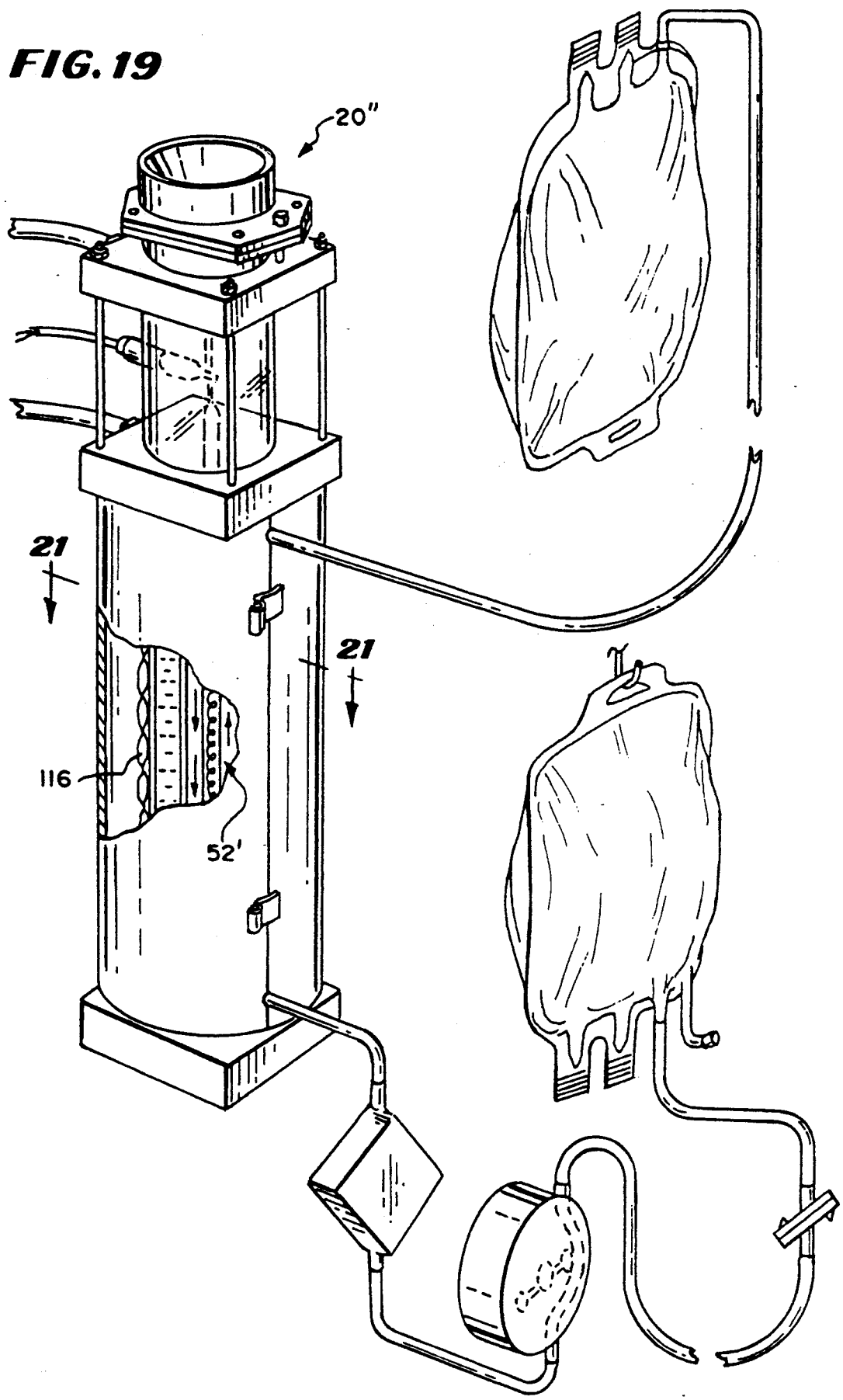
FIG. 19 is a perspective view, with portions broken away and in section of another system for treating fluids using photodynamic therapy that embodies the features of the invention.
Figure 20:
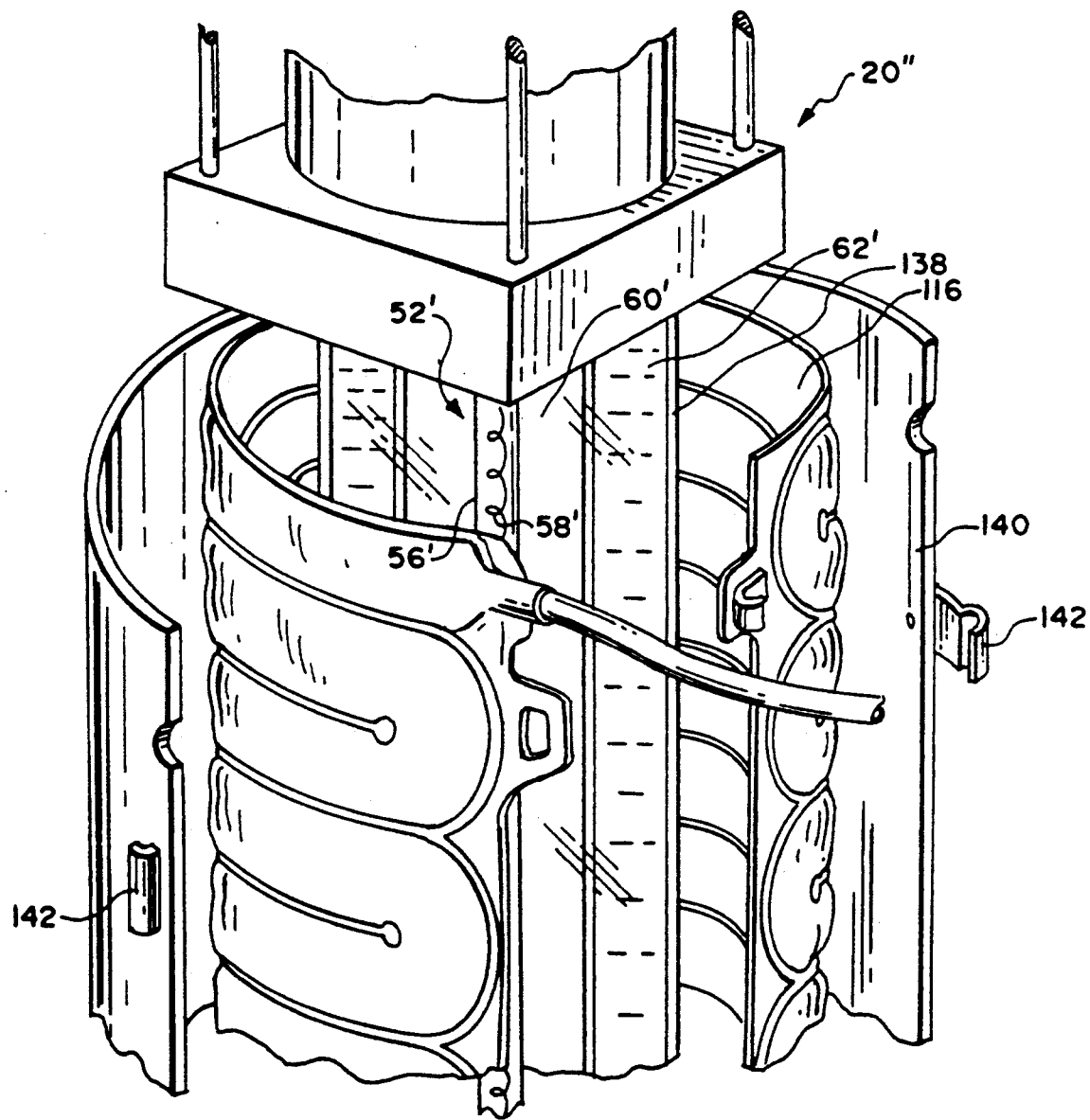
FIG. 20 is an enlarged perspective view of the top portion of the treatment device shown in FIG. 19.
Figure 22:
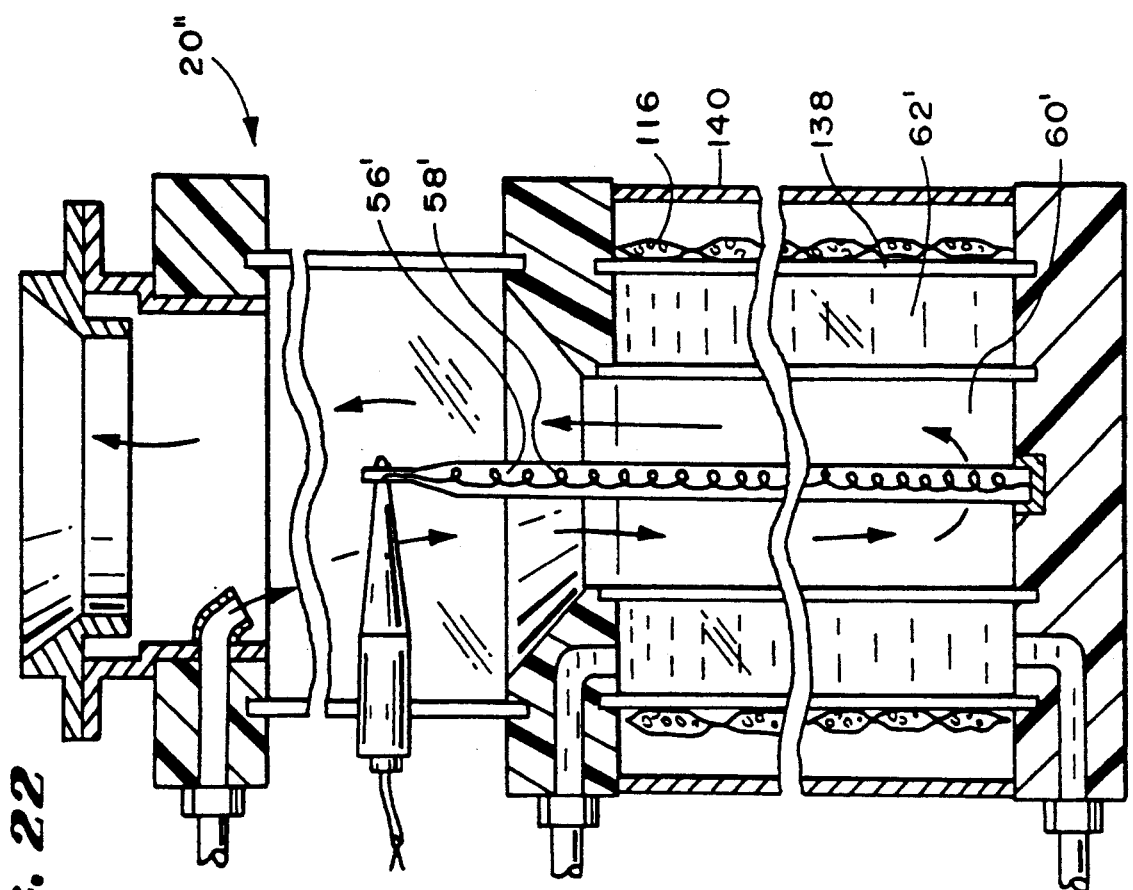
FIG. 22 is an enlarged side elevation view of the top portion of the treatment device shown in FIG. 19.
Figure 21:
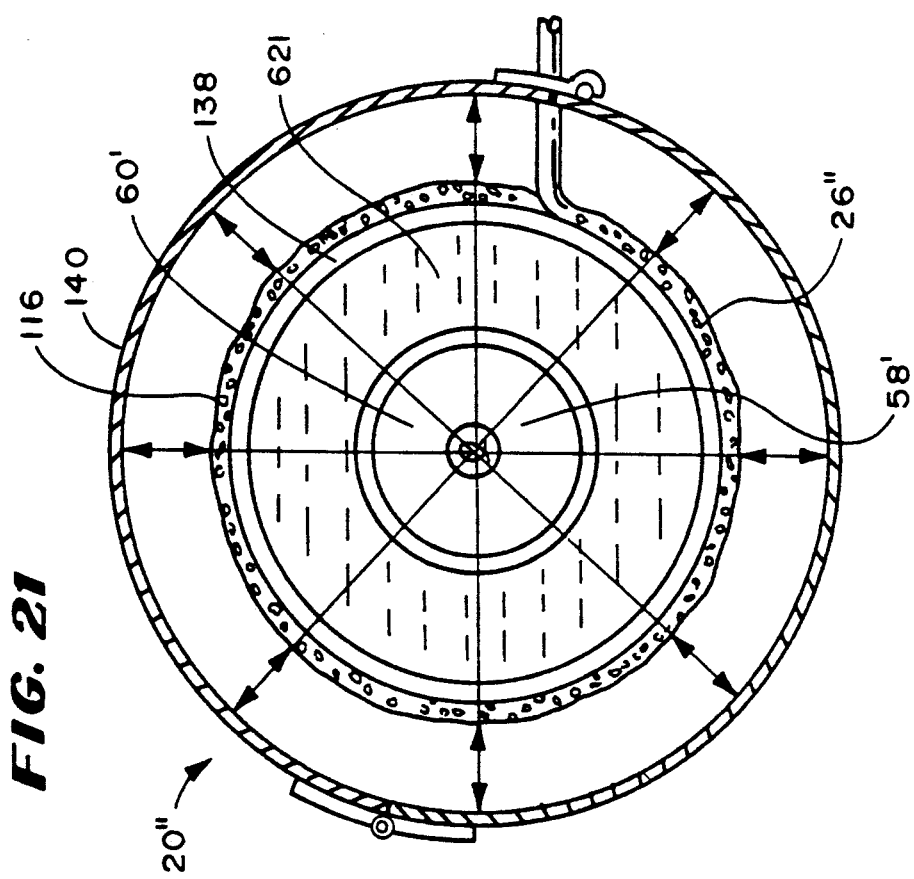
FIG. 21 is a top sectional view of the treatment device shown in FIG. 19 taken generally along line 21—21 in FIG. 19.

When wrapped upon the center platen 130, the bag 116 forms a treatment device 20' not unlike the treatment device 20 shown in FIGS. 1 to 13. As FIG. 18 shows, the device 20' has an arcuate gap 26' through which fluid is conveyed for treatment. The width of the gap 26' is determined by the configuration of the bag 116. When the outer platen 134 is used (as FIGS. 17 and 18 show), the spacing between the two platens 130 and 134 limits the maximum width of the gap 26'. The device 20' using the flexible bag 116 can be used in association with any of the treatment chambers 50 shown in FIGS. 1 to 13.

An alternative treatment device 20" that uses the flexible bag 116 is shown in FIGS. 19 to 22. This arrangement includes a generally elongated radiation source 52' that is much like the source 52 shown and previously described in FIGS. 1 to 3. Like the source 52 shown in FIGS. 1 to 3, the source 52' includes first and second chambers 60' and 62' that concentrically surround the bulb 56'. Air and water are circulated through these chambers 60' and 62' to cool the radiation source 52' in the manner previously described.

In the embodiment shown in FIGS. 19 to 22, the wall that forms the outer periphery of the second chamber 62' forms a first generally cylindrical platen 138. The flexible bag 116 is wrapped about this platen wall 138 (see FIG. 20) in the same fashion the bag 116 is wrapped about the center platen 130 shown in FIG. 16.

A second generally cylindrical platen 140 nests upon the first platen 138 to capture the bag in between. Releasable latches 142 hold the second platen 138 close. When captured between the two nested platens 138 and 140, the bag 116 conforms to their generally cylindrical shape (see FIG. 21). This creates the same relatively narrow, arcuately shaped gap 26" previously described. The maximum width of the treatment gap 26" is limited to the spacing between the two nested platens 138 and 140.

The first platen 138 is essentially transparent to the emitted radiation. This platen 138 thereby passes radiation from the source 52' directly into the adjacent side of the treatment chamber. The second platen 140 (like the elliptical reflectors shown in the preceding drawings) is made of a material that reflects the emitted radiation. This platen 140 thereby retains the emitted radiation within the treatment gap 26", directing radiation that passes out of the treatment chamber back into the gap 26".

The following example demonstrates the effectiveness of the systems that use relatively narrow arcuate gaps to process fluid undergoing photoactive therapy at relatively high flow rates.

EXAMPLE

Human red blood cell concentrates (at a hematocrit of about 55%) containing HSV-I virus were treated in accordance with the invention. Before, treatment, BPD was added at a concentration of 4 $\mu$g/ml. The red blood cell concentrate with the BPD added was pumped through a flexible treatment device as shown in FIG. 15 at a flow rate of 10 ml/min. The flexible treatment chamber was wrapped around a red incandescent bulb in an arrangement like that shown in FIG. 19. The viral load was reduced during the treatment by one order of magnitude (90%).

The features and advantages of the invention are set forth in the following claims.

We claim:

1. A device for treating a fluid carrying a contaminant to which a photoactive material has been bound, the material being activated by exposure to radiation within a prescribed wavelength range to eradicate the contaminant, the device comprising a treatment chamber shaped as an arcuate gap that extends between an outer cylindrical wall and an inner cylindrical wall spaced from the outer wall, the outer wall being essentially transparent to radiation within the prescribed wavelength to pass the radiation into the gap, the outer wall comprising a exterior wall of a generally flexible container and the inner wall comprising the opposite exterior wall of the flexible container and a generally cylindrical preformed interior platen about which the flexible container has been attached with the exterior container wall exposed.

2. A device according to claim 1
wherein the annular gap includes an inlet for receiving fluid and an outlet for discharging fluid.

3. A device according to claim 1
and further including an exterior platen that nests concentrically about the interior platen to capture the flexible container therebetween, the exterior platen being made of a material that is essentially transparent to the treatment radiation.

4. A system for treating a fluid carrying a contaminant to which a photoactive material has been bound, the material being activated by exposure to radiation within a prescribed wavelength range to eradicate the contaminant, the system comprising
a radiation chamber including
a generally elliptical reflective surface having at least one focal point,
means for establishing a source of radiation positioned within the reflective surface and having a selected wavelength within the prescribed range to activate the photoactive material bound to the contaminant, and
a treatment device located within the reflective surface at a focal point of the ellipse, the treatment device including a treatment chamber shaped as an arcuate gap that extends between an outer cylindrical wall and an inner cylindrical wall spaced from the outer wall, the outer wall being essentially transparent to radiation within the prescribed wavelength to pass the radiation into the gap, the outer wall comprising a exterior wall of a generally flexible container and the inner wall comprising the opposite exterior wall of the flexible container and a generally cylindrical preformed interior platen about which the flexible container has been attached with the exterior container wall exposed.

5. A system according to claim 4
wherein the means for establishing a source of radiation includes a single source of radiation.

6. A system according to claim 5
wherein the elliptical reflective surface includes two diametrically spaced focal points, and
wherein the single source of radiation is positioned at one of the focal points and the treatment chamber is position at the other focal point.

7. A system according to claim 4
wherein the means for establishing a source of radiation includes at least two sources of radiation.

8. A system according to claim 7
wherein each radiation source is discrete.

9. A system according to claim 8
wherein the radiation source includes a photodiode.

10. A system according to claim 4
wherein the elliptical reflective surface includes an open end extending along its minor axis and closed end spaced from the open end and including a focal point,
wherein means for establishing a source of radiation is located at the open end of the ellipse and faces in the direction of the closed end, and
wherein the treatment device is located in the closed end at the focal point.

11. A system according to claim 10
wherein the means for establishing a source of radiation includes at least two sources of radiation.

12. A system according to claim 11
wherein each radiation source is discrete.

13. A system according to claim 10
wherein the sources of radiation include photodiodes.

14. A system for treating a fluid carrying a contaminant to which a photoactive material has been bound, the material being activated by exposure to radiation within a prescribed wavelength range to eradicate the contaminant, the system comprising
a treatment device including a treatment chamber shaped as an arcuate gap that extends between an outer cylindrical wall and an inner cylindrical wall spaced from the outer wall, the inner wall being essentially transparent to radiation within the prescribed wavelength to pass the radiation into the gap, and
a radiation chamber including means for establishing a source of radiation positioned adjacent the inner wall of the treatment chamber and having a selected wavelength within the prescribed range to activate the photoactive material bound to the contaminant, the inner and outer walls comprising the exterior walls of a generally flexible container, and the inner wall further comprises a generally cylindrical platen that surrounds the source of radiation and about which the flexible container has been attached, the platen being made of a material essentially transparent to the radiation emitted by the source.

15. A system according to claim 14
wherein the radiation chamber further includes a reflective surface surrounding the outer exterior wall of the flexible container.

* * * * *